US00PP27289P2

(12) United States Plant Patent
Doguet et al.

(10) Patent No.: US PP27,289 P2
(45) Date of Patent: Oct. 18, 2016

(54) ZOYSIAGRASS PLANT NAMED 'M85'

(50) Latin Name: ***Zoysia matrella* (L.) Merr.**
Varietal Denomination: M85

(71) Applicants: David Doguet, Pleasanton, TX (US); Daric Alan Doguet, Jourdanton, TX (US); Virginia Gail Lehman, Lebanon, OR (US)

(72) Inventors: David Doguet, Pleasanton, TX (US); Daric Alan Doguet, Jourdanton, TX (US); Virginia Gail Lehman, Lebanon, OR (US)

( * ) Notice: Subject to any disclaimer, the term of this patent is extended or adjusted under 35 U.S.C. 154(b) by 0 days.

(21) Appl. No.: 14/545,601

(22) Filed: May 29, 2015

(51) Int. Cl.
*A01H 5/12* (2006.01)

(52) U.S. Cl.
USPC ..... Plt./390

(58) Field of Classification Search
USPC ..... Plt./390
See application file for complete search history.

*Primary Examiner* — Annette Para

(57) ABSTRACT

An asexually reproduced variety of perennial zoysiagrass with a unique combination of morphological characters including medium fine leaf texture, short leaf length, low canopy height, and medium stiff leaf flexibility.

2 Drawing Sheets

Latin name of the genus and species of the plant claimed: The present invention relates to the genus and species *Zoysia matrella* (L.) Merr.

Variety denomination: 'M85'.

CROSS-REFERENCE TO RELATED APPLICATIONS

"Not Applicable"

STATEMENT REGARDING FEDERALLY SPONSORED RESEARCH OR DEVELOPMENT

"Not Applicable"

BACKGROUND OF THE INVENTION

Field of Invention

The present invention relates to a new and distinct asexually reproduced variety of perennial zoysiagrass (*Zoysia matrella* (L.)) Merr.

BRIEF SUMMARY OF THE INVENTION

This invention relates to a new and distinct perennial zoysiagrass cultivar identified as 'M85' zoysiagrass (herein referred to as 'M85'). The inventors, David L. Doguet, Daric A. Doguet, and Virginia G. Lehman, discovered 'M85' under cultivated conditions near Poteet, Tex. in a collection of seedling plants. The seedling plants originated from proximity crosses among 'Zeon' (U.S. Plant Pat. No. 13,166), 'L1F' (U.S. Plant Pat. No. 25,203), 380-1 (unpatented), and 29-2 B9 (unpatented). 'M85' was identified in 2011 as a distinctly different vegetative patch or clonal plant differing from the surrounding plants. 'M85' showed less seedheads than 'Diamond' (U.S. Plant Pat. No. 10,636) and less dollar spot than surrounding grasses in fall quality ratings. The inventors asexually reproduced 'M85' by taking vegetative cuttings of stolons and rhizomes, cutting the rhizomes and stolons into segments, each with a vegetative bud, and rooting them in potting media. 'M85' zoysiagrass will be used as a turfgrass suitable for home lawns, sports fields, and golf courses.

For purposes of registration under the "International Convention for the Protection of New Varieties of Plants" (generally known by its French acronym as the UPOV Convention) and noting Section 1612 of the Manual of Plant Examining Procedure, it is proposed that the title of the invention is Zoysiagrass plant named 'M85'.

BRIEF DESCRIPTIONS OF THE ILLUSTRATIONS

Figure 1:
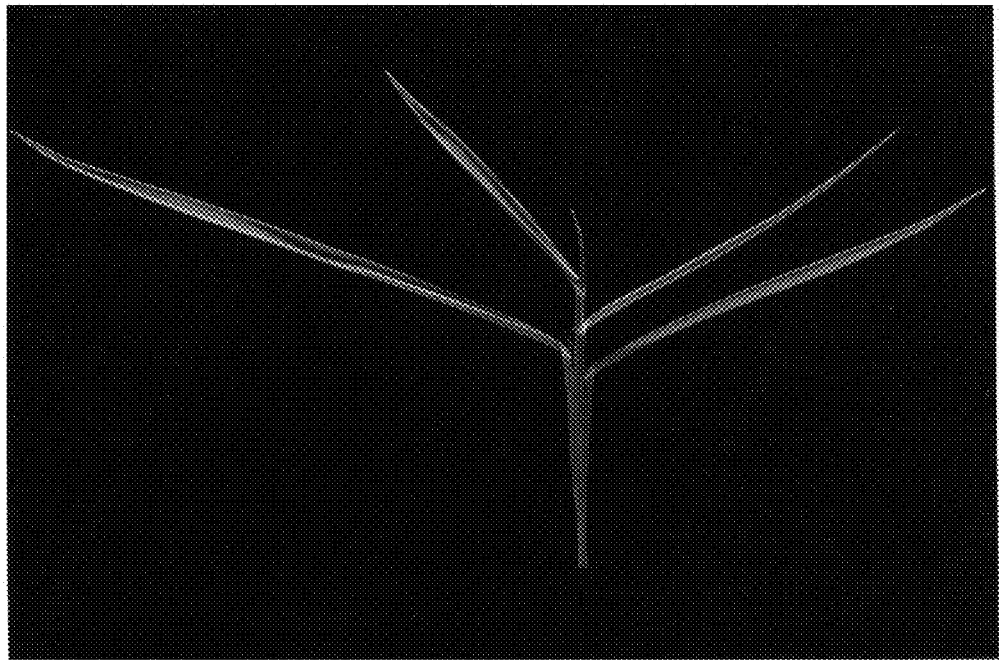
Figure 2:
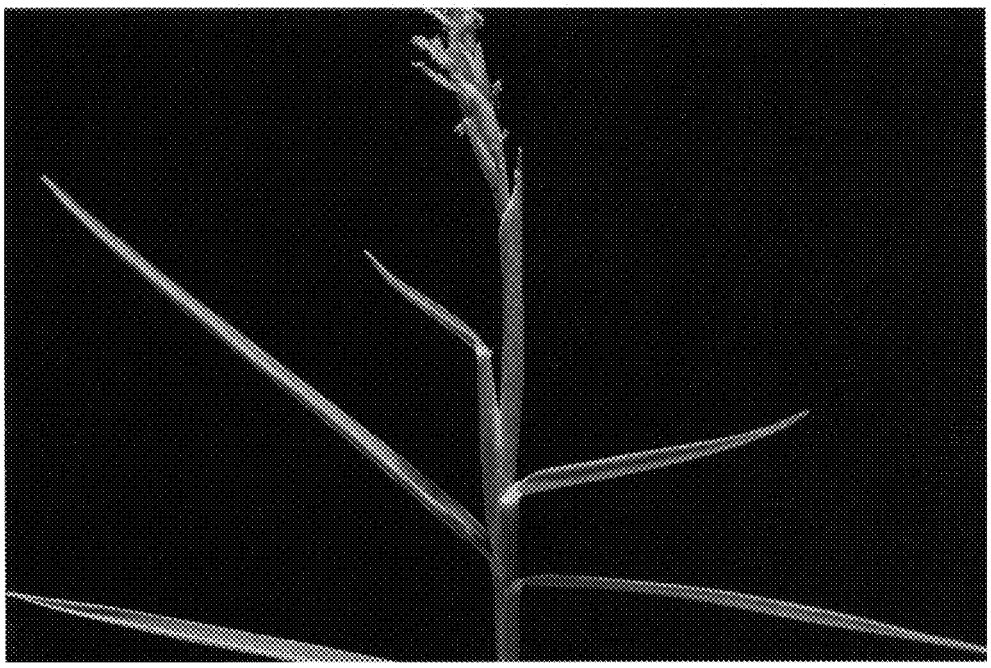

FIG. 1. Tiller of 'M85' zoysiagrass.
FIG. 2. Inflorescence of 'M85' zoysiagrass.

COMPLETE BOTANICAL DESCRIPTION OF THE VARIETY

'M85' was characterized in greenhouse and field conditions. 'M85' is a unique variety of zoysiagrass (*Zoysia matrella* (L.)) Merr. that was discovered under cultivated conditions. The inventors, David L. Doguet, Daric A. Doguet, and Virginia G. Lehman, discovered 'M85' near Poteet, Tex. in a collection of seedling plants. The seedling plants originated from proximity crosses with 'Zeon' (U.S. Plant Pat. No. 13,166), 'L1F' (U.S. Plant Pat. No. 25,203), 380-1 (unpatented), and 29-2 B9 (unpatented). Both unpatented plants originated from field grown open pollinated crosses between 'VJay' (unpatented), '6136' (U.S. Plant Pat. No. 17,808), and 'JaMur' (U.S. Plant Pat. No. 13,178) *zoysia* plants. The seed was bulked from the four parents, each individual seed was planted in a pot, and plants subsequently transplanted to the field. 'M85' was identified in 2011 as a distinctly different vegetative patch or clonal plant. 'M85' showed less seedheads than 'Diamond' (U.S. Plant Pat. No. 10,636) and less dollar spot than surrounding grasses in fall quality ratings. The plants were located in USDA Plant Hardiness Zone 8. The inventors asexually reproduced 'M85' in both Poteet, Tex. and Lebanon, Oreg. by taking vegetative cuttings of stolons and rhizomes, cutting the rhizomes and stolons into segments, each with a vegetative bud, and rooting them in potting media. Planting of the rooted material provided planting stock for studying performance and for comparison of morphological characters after propagation. 'M85' has been propagated by rhizomes, stolons, tillers, and sod. Asexually reproduced plants of 'M85' have remained stable and true to type through successive generations of propagation. No seedling establishment from 'M85' has been noticed in either greenhouse or field studies.

'M85' is a perennial zoysiagrass that spreads by both stolons and rhizomes. Characteristics of 'M85' measured in 2015 were taken from plants that were approximately 8 months in age. The greenhouse was located near Lebanon, Oreg., with a nighttime low temperature of 50 degrees F., and daytime high of 80 degrees F., and a minimum soil temperature of 77 degrees F. The plants were grown under natural day length without supplemental lighting. The plants were fertilized with the equivalent of 1 pound of actual N per month, using a soluble fertilizer of 20-20-20 in four equal soluble applications per month.

'M85' has a medium fine leaf texture with a more narrow leaf than 'Y2' (Table 1). 'Y2' was originally classified as a medium textured grass but the continued development of fine textured zoysiagrasses may make the relative texture re-defined as medium coarse. 'M85' has an absence of leaf hairs similar to 'Diamond', both of which are in contrast to 'Zorro' which has many leaf surface hairs (Table 2). 'M85' has a youngest and second youngest stolon node not statistically different from Zorro (Table 3) but with shorter 1-2, 2-3, and 3-4 stolon internode lengths than 'Zorro' (Table 3). 'M85' has a short unmown canopy height that is illustrated by a short leaf (Table 1). The maximum unmown leaf crown height of 'M85' is at the maximum inflorescence height in the leaf canopy. 'M85' has shown high quality turf ratings when evaluated in replicated plantings in Poteet, Tex. (Table 4). 'M85' has shown superior color ratings compared to 'Zeon', with a finer leaf texture under mowing than both 'Zeon' and 'L1F'.

'M85' has not shown susceptibility to the zoysiagrass mite when tested at Poteet, Tex., where susceptible varieties have shown the coachwhip leaf symptoms of the mite. 'M85' has shown good turfgrass performance and temperature adaptation when tested as far north as Athens, Ga., USDA hardiness zone 8a, which would extend the area of adaptation for 'M85' in a line from northern Georgia across central Texas in an East/West line and on a North/South line from Atlanta, south through Mexico. 'M85' will be limited only by winter survival in colder regions, and has shown severe winter damage in field plantings in Oregon during the winter of 2013-14. 'M85' is similar to most medium fine textured zoysiagrasses in water use demands as shown in test situations near Poteet, Tex. 'M85' is adapted from sandy to heavier loam soil textures and from slightly acid to slightly alkaline soil pH.

TABLE 1

Leaf blade widths and lengths and texture class of selected zoysiagrass cultivars, measured under greenhouse conditions in Lebanon, OR, 2015.

| Variety | Length, 2nd youngest crown leaf cm | Width, 2nd youngest crown leaf mm | Leaf Texture Class Rating |
|---|---|---|---|
| 'M85' | 1.86 | 2.11 | Medium-Fine |
| 'Zorro' | 2.33 | 1.76 | Medium |
| 'Diamond' | 2.51 | 1.3 | Fine |
| 'Y2' | 3.3 | 2.76 | Medium-coarse |
| Lsd, p = 0.05 | 0.9 | 0.39 | |

TABLE 2

Adaxial leaf hair presence or absence of selected zoysiagrass cultivars, measured under greenhouse conditions in Lebanon, OR, 2015.

| | Leaf hair, adaxial Presence/Variety Number |
|---|---|
| 'M85' | Absent |
| 'Diamond' | Absent |
| 'Zorro' | Many |

TABLE 3

Stolon characters of selected zoysiagrass cultivars, measured under greenhouse conditions in Lebanon, OR, 2015.

| Variety | Thickness $1^{st}$ youngest stolon node mm | Thickness 2nd youngest stolon node mm | Stolon Internode length, $1^{st}$ to $2^{nd}$ node cm | Stolon Internode length, 2nd to $3^{rd}$ node cm | Stolon Internode length, 3rd to 4th node cm |
|---|---|---|---|---|---|
| 'M85' | 2.01 | 1.68 | 1.5 | 1.5 | 1.42 |
| 'Zorro' | 1.83 | 1.67 | 2.67 | 2.9 | 2.53 |
| 'Diamond' | 1.11 | 1.28 | 1.26 | 1 | 0.93 |
| 'Y2' | 2.4 | 2.37 | 2.47 | 2.57 | 2.07 |
| Lsd, p = 0.05 | 0.56 | 0.57 | 0.61 | 0.92 | 0.94 |

TABLE 4

Turf quality ratings taken in August in Poteet, TX in 2014, with turf mowed at fairway heights.

| Variety | Cover ^^ | Quality # | Texture $ | Color ^ |
|---|---|---|---|---|
| 'M85' | 3.3 | 5.6 | 8.7 | 8.3 |
| 'Zeon' | 4.3 | 5.4 | 6.7 | 6 |
| 'L1F' | 3.3 | 5.4 | 7.7 | 7.3 |
| CV | 28.6 | 10.06 | 6.93 | 9.05 |
| Lsd, p = 0.05 | 1.79 | 0.89 | 0.81 | 1.18 |

^^ Cover rated on a scale of 1-9, 9 = most cover.
Quality rated on a scale of 1-9, 9 = best quality.
$ Texture rated on a scale of 1-9, 9 = finest texture.
^ Color rated on a scale of 1-9, 9 = darkest green.

COMPLETE BOTANICAL DESCRIPTION OF THE VARIETY

Origin: 'M85' is a cultivar of a single clone of zoysiagrass discovered under cultivated conditions in a Poteet, Tex. planting of zoysiagrass clones derived from a collection of seedling plants. The seedling plants originated from proximity crosses among 'Zeon' (U.S. Plant Pat. No. 13,166), 'L1F' (U.S. Plant Pat. No. 25,203), 380-1 (unpatented), and 29-2 B9 (unpatented). The unpatented parents of 'M85' originated from field grown open pollinated crosses between 'VJay' (unpatented), '6136' (U.S. Plant Pat. No. 17,808), and 'JaMur' (U.S. Plant Pat. No. 13,178) *zoysia* plants. 'M85' was identified in 2011 as a distinctly different vegetative patch or clonal plant. 'M85' differed from the surrounding plants in less seedheads than 'Diamond' (U.S. Plant Pat. No. 10,636) and less dollar spot than surrounding grasses in fall quality ratings.

Classification: *Zoysia matrella* (L.) Merr.

Growth habit: 'M85' is a perennial plant that spreads by stolons and rhizomes and produces a dense, very fine turfgrass. The inflorescence of 'M85' is a terminal spike-like raceme, with spikelets on short pedicels.

Leaf blade: Rolled in the bud, flat surface.

Leaf blade pubescence: No hairs on abaxial or adaxial leaf.

Leaf margin pubescence: Barbellate margins. 'Palisades' has some barbellate margin to a small degree, but not as prominent or regular as M85.

Leaf sheath pubescence: Absent except for long hairs at mouth of sheath, and a ring of short hairs inside the sheath where it attaches to the stem.

*'M85' mean length sheath mouth hairs at side of sheath.*—1.5 mm; inside sheath ring of hairs: 0.5 mm.

Leaf blade margin: 'M85'=slight roughness.

Leaf blade veins: Prominent.

Leaf blade flexibility (softness): Medium soft compared to 'Diamond' with a stiff leaf.

Vegetative leaf, 2nd youngest vegetative leaf:

*Blade length range.*—'M85': 24 to 14 mm, mean length: 18.7 mm.

*Blade width mean.*—'M85': 1.9 mm to 2.25 mm, mean width: 2.11 mm.

Sheath length, $4^{th}$ youngest vegetative leaf:

*Mean length 'M85'.*—8.5 mm.

Stolon leaf angle, third youngest leaf: 'M85': 75; 'Diamond': 52 (by reference).

Inflorescence characters:

*Culm total length, including floral area to node below flag leaf.*—2.0 cm. Length of stem of inflorescence: mean of 12.0 mm. Floral area length: mean of 8 mm.

*Culm width, stem thickness, base of floral area.*—0.5 mm.

*Anther length.*—1.5 mm.

*Floret (seed) length.*—Range 2.25 to 2.5 mm.

*Floret (seed) width.*—Mean of 0.7 mm.

*Node thickness, node below flag leaf.*—1.0. mm.

*Pedicel length.*—0.85 mm.

*Flag leaf length.*—'M85': 0.9 cm.

*Flag leaf width.*—'M85': 1.7 mm.

Mature plant height, unmown in greenhouse, including inflorescence.—10 cm.

Color notations, vegetative characters, based on The R.H.S. Colour Chart (light quality, photoperiod, and general growth of the plants affect color notations):

*Leaf blade color adaxial leaf surface.*—137 A green.

*Leaf blade color abaxial leaf surface.*—137A green.

*Stolon color.*—158A yellow-white, 138B green.

Color notations, floral characters, based on The R.H.S. Colour Chart (light quality, photoperiod, and general growth of the plants affect color notations):

*Culm stalk.*—137 D green.

*Stigma.*—155B greyed yellow.

*Anther color, fresh.*—155 B, 160C greyed yellow.

*Anthers, mature, dried.*—163C greyed orange.

Turf quality in August (rated 1-9, 9 best): 'M85': 5.6; 'Zeon': 5.4.

We claim:

1. A new and distinct variety of zoysiagrass plant, substantially as described and illustrated herein, characterized particularly by a unique combination of morphological characters.

* * * * *